United States Patent [19]

Kawan

[11] Patent Number: 4,965,071

[45] Date of Patent: Oct. 23, 1990

[54] WRINKLE MASKING COMPOSITION OF SODIUM POLYSTYRENE SULFONATE AND PROCESS FOR USE

[75] Inventor: Antoine Kawan, Washington, D.C.

[73] Assignee: The Gillette Company, Boston, Mass.

[21] Appl. No.: 259,713

[22] Filed: Oct. 19, 1988

[51] Int. Cl.$^5$ ............................................. A61K 7/02
[52] U.S. Cl. ..................................... 424/401; 424/69;
424/78; 424/484; 424/486; 514/844; 514/944
[58] Field of Search .................. 424/401, 78, 69, 484, 424/486; 514/844, 944

[56] References Cited

U.S. PATENT DOCUMENTS

| | | | |
|---|---|---|---|
| 2,936,245 | 5/1960 | Osipow et al. | 106/189 |
| 3,444,291 | 5/1969 | Bivans | 424/63 |
| 3,523,998 | 8/1970 | Feinstone et al. | 424/78 |
| 3,819,825 | 6/1974 | Goodwin | 424/63 |
| 3,862,309 | 1/1975 | Krochock | 424/63 |
| 3,949,741 | 4/1976 | Hofman | 128/76 B |
| 4,126,142 | 11/1978 | Saute | 132/7 |
| 4,255,416 | 3/1981 | Gillespie | 424/80 |
| 4,362,715 | 12/1982 | Strianse et al. | 424/78 |
| 4,432,347 | 2/1984 | Calvin | 128/1 R |
| 4,534,961 | 8/1985 | Liff | 424/63 |
| 4,536,405 | 8/1985 | Nara et al. | 514/781 |
| 4,591,501 | 5/1986 | Cioca | 514/844 X |
| 4,659,562 | 4/1987 | Arraudeau et al. | 424/63 |
| 4,777,041 | 10/1988 | Mercado | 424/78 |
| 4,818,751 | 4/1989 | Ibe | 514/844 X |
| 4,851,521 | 7/1989 | della Valle et al. | 514/844 X |

FOREIGN PATENT DOCUMENTS

| | | | |
|---|---|---|---|
| 0106193 | 4/1984 | European Pat. Off. | 514/844 |
| 2512651 | 3/1983 | France . | |
| 2543826 | 10/1984 | France . | |

OTHER PUBLICATIONS

Irma Shorell, "Years Younger", Packaging Container.
Calvin Laboratories "Eye Lift", Advertising Brochure.
Dermablend Cover Cream, "Product Advertisement".
De Navarre "Wrinkle Smoothers'", *The Chemistry and Manufacture of Cosmetics*, 2nd Ed., vol. 4, pp. 1369-1378, 1975.
Laboratoires Serobiologiques, "Technical and Advertising Dossier", Oct. 1985.
Centerchem, Inc. "Technical Bulletin" AMIHOPE$^R$LL.

Primary Examiner—Thurman K. Page
Attorney, Agent, or Firm—Burns, Doane, Swecker & Mathis

[57] ABSTRACT

A wrinkle masking composition and process for use which temporarily eliminates fine line wrinkles and blemishes of the skin by filling, covering or otherwise effectively masking them. The composition includes a film forming polymer, a plasticizer for the polymeric matrix, a biopolymeric modifier and a filler including aluminosilicate. Optionally, the composition includes cosmetic additives, for example, pigments, rheology control agents, binders and preservatives. By molding itself to the skin, the present invention is compatible with and can be worn under makeup without cracking or peeling.

49 Claims, No Drawings

WRINKLE MASKING COMPOSITION OF SODIUM POLYSTYRENE SULFONATE AND PROCESS FOR USE

BACKGROUND OF THE INVENTION

The present invention relates to a wrinkle masking composition and process for use. In particular, the present invention relates to a wrinkle masking composition for cosmetic application and process for use.

Many ideas have been proposed in the art of wrinkle masking. None has resulted in a composition that can effectively cover and temporarily eliminate the appearance of fine line wrinkles.

In the past, wrinkle smoothing products have appeared in the market place from time to time, but were soon withdrawn due to poor performance. These earlier products were based on bovine serum albumin, which is a protein derived from the fractionation of cattle blood, and were marketed by leading cosmetic houses. These protein based products smoothed the face because of the skin tightening effect of the serum albumin, but failed to adequately mask the fine lines and wrinkles. Makeup could not be easily applied over them. Other problems included sensitization of the skin due mainly to the serum albumin protein, malodor upon product deterioration, and high cost due to the limited sources of supply.

More recently, the wrinkle masking product category came back to light with the introduction of a few wrinkle smoothers which claimed to be improved. These new products were based on clays and gums and had some advantages over their earlier predecessors. Even more recently, products have appeared on the market which claim to mask and cover wrinkles. These recently introduced wrinkle masking products include: sodium silicate compositions having a pH of about 12, accordingly not recommended for delicate or damaged skin and upon application form a chalky film, which is highly susceptible to cracking; wrinkle masking tape, typically a two-sided adhesive tape for application to the upper eyelid, which serves as an eyelift to produce a younger look. This latter product is difficult to apply and fails to present a satisfactory solution to the problem of masking wrinkles. Still more recently several products that claim antiwrinkle effects have started to appear; however, these products do not involve a temporary cover/masking mechanism but rather involve a skin penetrating treatment that starts to work after several weeks of use. These are unrelated to the subject matter of the present invention. A large number of compositions have been patented in the art of wrinkle masking, but few have resulted in an effective commercial product.

U.S. Pat. No. 4,362,715 to Strianse et al discloses a cosmetic composition composed of an organic polymer of acidic functionality and a zeolite. Additional ingredients include carboxy-methylcellulose, pigments, alcohols, glycols, surfactants, clays, and the like.

U.S. Pat. No. 3,862,309 to Krochock discloses sodium polystyrene sulfonate for use as a film-former to smooth wrinkles. The aqueous solution also includes a surfactant, alcohol, pigments or dyes, and other cosmetic materials such as algin, magnesium aluminum silicate, and the like.

U.S. Pat. No. 3,819,825 to Goodwin discloses keratinaceous protein extracted from hydrolyzed chicken feathers, animal hair and hoofs. The protein is blended with large amounts of colloidal silica to produce skin conditioners and temporary wrinkle removers.

U.S. Pat. No. 4,126,142 to Saute discloses a multiple step process in which a sodium polystyrene sulfonate film is applied to the skin and allowed to dry. The dried film is removed from the skin creating a cleansing action and subsequently is replaced by a moisture barrier formulation.

U.S. Pat. No. 3,523,998 to Feinstone et al. discloses water soluble film-formers for use as wrinkle smoothers. Suitable polymers include mixtures of dextran, ethylene-maleic anhydride copolymers and sodium carboxymethylcellulose.

U.S. Pat. No. 4,255,416 to Gillespie claims improvement over the Krochock patent. Sodium silicate and a second water based polymer are added to the sodium polystyrene sulfonate film former for use as a skin firming composition.

U.S. Pat. No. 4,534,961 to Liff discloses petrolatum and microcrystalline wax in various proportions for use as a makeup base.

U.S. Pat. No. 4,536,405 to Nara et al. discloses a makeup composition containing ethylhydroxyethylcellulose and a hydrocarbon resin. The final product is claimed to have superior water resistance properties and good skin adhesion.

U.S. Pat. No. 3,949,741 to Hofmann teaches a method for wrinkle reduction using a pressure sensitive adhesive appliance. In accordance with the method, the appliance is tightly applied over wrinkled areas of the face and kept in place for four hours. Upon removal the appliance strips dead cells from the face to create a smoother, younger look. The disclosed appliance is based on polymeric films such as polyethylenes, polypropylenes, polyurethanes, and the like.

Many patents have disclosed adhesive backed tapes of various forms and designs for use in covering wrinkles. One example is U.S. Pat. No. 4,432,347 to Clavin which discloses a two-sided tape for use around the eye to affect a pull or a lift; this has resulted in the commercial product discussed above. Several European patents, including French Pat. Nos. 2,543,826 to Micheau and 2,512,651 to Pere-Lahaille, have also disclosed various designs and forms of tapes to cover facial wrinkles.

Numerous items have been patented for the covering or prevention of wrinkles. These items include:

* A wire-formed facial wrinkle remover with multiple wire loops to permit shaping.
* Mask-forming skin preparations based on water hardenable gypsum ($CaSO_4$) to remove wrinkles and remodel double chins.
* An eye-wrinkle remover based on a pad specially designed for holding an astringent.
* Compositions based on RNA and DNA.
* Compositions containing keratic proteins and colloidal $SiO_2$.
* Medicaments containing $HgCl_2$.
* A wrinkle remover based on form-fired gypsum.
* A variety of compositions containing water-soluble polymers.
* Compositions containing glycoproteins and a hydroscopic excipient.
* Compositions containing bovine embryo cells, DNA and deoxyribonucleic acid.
* Surgical techniques.
* Electric wrinkle removal treatments.

* A pressure sensitive adhesive patch specially stiffened to hold skin well tensioned.
* Cream containing alpha-dihydroxyphenylalanine, beeswax emulsion, Vitamin-D, and Vitamin-E.
* Thin films of rubber and/or plastic delivered on the exact site by a special process.
* Phytosterol containing compositions.
* A specially designed surgical drape assembly coated with a special adhesive.
* Acrylic film patches coated with an acrylic adhesive.
* Fomes Japonicies extract to remove wrinkles and spots.
* A treatment using a low electric pulse generation having a repetition rate of 100–500 Hz.
* Pseudoplastic compositions containing carboxyvinyl polymers and zeolites.
* Sunflower extract.
* Pharmaceutical compositions containing antibody serum. The technical literature supplied by raw material vendors provides two general purpose systems, namely: modifications of the Krochock system and a system which uses serum albumin. This latter system includes many modifications in which the serum albumin is compounded with film-formers such as polyvinylpyrrolidone (PVP) and carboxymethylcellulose (CMC). These serum albumin compositions produce a skin tightening effect causing the skin to feel smooth for a short time. Various forms of this formulation are described in DeNavarre, M. G., "Wrinkle Smoothers" *The Chemistry and Manufacture of Cosmetics,* 2nd ed.; deNavarre, M. G., Ed.; Continental Press: Orlando, Fla., 1975; 4, pp. 1369–78. One example of a general purpose formulation based on bovine serum albumin is composed of approximately 30% weight by weight (w/w) albumin bovine serum, 69.9% (w/w) aqueous Phylderm Filatov ® (an amino protein complex) and 0.1% (w/w) Kathon ® CG (a preservative). After application of this composition the skin has a smooth feel, but the fine wrinkle lines on the skin are not covered.

The art lacks a cosmetic composition that can effectively mask and temporarily eliminate the appearance of fine line wrinkles. A composition having these properties would provide an excellent solution to the age-old problem of maintaining a healthy and attractive youthful look.

It is therefore an object of the present invention to provide a cosmetic composition that temporarily eliminates fine line wrinkles and blemishes on the skin by filling, covering or otherwise effectively masking them.

It is also an object of the present invention to provide a wrinkle masking composition having good hiding power that is easy to apply to all types of skin and then to remove.

It is a further object of the present invention to provide a wrinkle masking composition having a short drying time.

Another object of the present invention is to provide an economical wrinkle masking composition that is compatible with makeup when applied underneath.

A further object of the present invention is to provide a wrinkle masking composition that is comfortable to wear, allows the skin to breathe and is pleasant with repeated use on all skin types.

Another object of the present invention is to provide a wrinkle masking composition that is resistant to skin secretions such as sebum and perspiration.

A further object of the present invention is to provide a wrinkle masking composition that can be worn for at least about 6 hours with acceptable results.

Another object of the present invention is to provide a wrinkle masking composition that adapts to changes in facial expressions and movement without cracking or peeling by molding itself to the skin.

A further object of the present invention is to provide a process for applying a cosmetic composition that temporarily eliminates fine line wrinkles and blemishes on the skin.

SUMMARY OF THE INVENTION

In accordance with an aspect of the present invention, these objects are achieved by a wrinkle masking composition which includes a film forming polymer, a plasticizer for the polymeric matrix, a biopolymeric modifier and a filler. The composition optionally includes cosmetic additives, e.g., pigments, rheology control agents, binders and preservatives.

In accordance with a further aspect of the present invention, these objects are achieved by a process for covering or masking the fine line wrinkles of the skin.

DETAILED DESCRIPTION OF THE PREFERRED EMBODIMENTS

The present invention is a wrinkle masking composition including a film forming polymer, a plasticizer for the polymeric matrix, a biopolymeric modifier and a filler. The composition can optionally include pigments, colorants, additional fillers, preservatives, rheology control agents, blending agents and other additives as needed. The cosmetic composition temporarily eliminates the appearance of fine line wrinkles and blemishes on the skin by filling, covering or otherwise effectively masking them.

The film forming polymer of the present invention is water soluble. The water soluble film forming polymer is a binder and matrix for the other ingredients of the composition. The water soluble film forming polymer is compatible with skin and forms a strong matrix which holds the other ingredients of the composition together and over the skin. Sodium polystyrene sulfonate is a suitable polymeric film former which forms a matrix and provides excellent binding to the skin. Sodium polystyrene sulfonate is commercially available from the National Starch and Chemical Corporation marketed under the name Flexan 130 ® (30% solids). Sodium polystyrene sulfonate is added in an amount of from about 0.3 to about 1.8%, preferably about 0.6 to about 0.75%, of the total composition based on 100% solids. Additional aqueous film forming water soluble polymers for use in combination with the matrix forming polymer include carboxymethyl cellulose, cellulosic ethers and PVP polymers; these provide further reinforcement of the basic film matrix composition. A suitable carboxymethyl cellulose is commercially available from Hercules, Inc. marketed under the name CMC-7MF ® (medium viscosity pharmaceutical grade). Carboxymethyl cellulose is added in an amount from about 1 to about 3%, preferably from about 1.5 to about 2.25%, of the total composition based on 100% solids. The total film forming polymer is from about 1.3 to about 4.8%, preferably from 2.1 to about 3%, of the total composition based on 100% solids.

The water soluble polymeric films are plasticized with agents such as glycols and polyols. Suitable plasticizers include glycerin, propylene glycol, hexylene glycol and the like. Plasticizers are based on the total binder content and added in an amount of from about 10 to about 30%, preferably from about 15 to about 25%, of the total composition based on 100% solids.

The biopolymeric modifier derived from skin improves the overall flexibility of the composition, promotes better adherence of the film to skin and allows the film to adapt to dimensional changes associated with changing skin configuration. The biopolymeric modifier in combination with the polymeric film former imparts to the composition skin compatibility, accordion-like mechanical properties and skin-like tactile feel. The resultant skin-like character of the film enables the film to adapt to skin movement, e.g., facial expressions, without breaking or falling off. Thus the use of a biopolymeric modifier in the composition avoids mechanical problems, in particular it prevents the film from being dry, chalky, or brittle and allows the film to follow the movement of the skin without cracking or falling off. Suitable biopolymeric modifiers include elastin; collagen; simple polysaccharides or glycogen; complex polysaccharides or glycosaminoglycans, such as hyaluronic acid and sulphuric chondroitin acid. The latter modifier, namely simple polysaccharides or glycogen and complex polysaccharides or glycosaminoglycans are available as the commercial concentrate Dermosaccharides ® LS-ST. The biopolymeric modifier is from about 0.0025 to about 1.94%, preferably from about 0.0075 to about 1.25%, of the total composition based on 100% solids. In a preferred embodiment hyaluronic acid is added in an amount of from about 0.0025 to about 0.02%, preferably from about 0.005 to about 0.0125%, and more preferably from about 0.0075 to about 0.01%, of the total composition based on 100% solids. Elastin is added in an amount of from about 0.1 to about 0.7%, preferably from about 0.2 to about 0.6%, and more preferably from about 0.4 to about 0.55%, of the total composition based on 100% solids. Collagen is added in an amount of from about 0.003 to about 0.021%, preferably from about 0.006 to about 0.018%, and more preferably from about 0.009 to about 0.015%, of the total composition. Specific forms of these ingredients are commercially available from Centerchem, Inc. marketed under the name Hydrolastan ® (partially hydrolysated elastin); and Gattefosse Corp. marketed under the name Pancogene-S ® (0.3% soluble collagen). The biological complex, Dermosaccharides ® LS-ST (12% solution) marketed by Laboratories Serobiologiques, Inc. is prepared from connective tissue, epithelial tissue and vitreous humor of the eye. The complex exhibits many biological and cosmetodynamic properties of skin, including playing a role as a hydrating agent, a cohesion enhancer, a cutaneous lubricating emollient and softening agent, a stimulus for fibroblast growth, a reinforcer for tonicity, and in improving biophysical properties, i.e., elasticity, viscoelasticity and plasticity. In a preferred embodiment Dermosaccharides ® LS-ST (12% aqueous solution) is added in an amount of from about 0.24 to about 1.2%, preferably from about 0.36 to about 0.96%, and more preferably from about 0.6 to about 0.72%, of the total composition based on 100% solids.

The filler contains sodium aluminosilicate, e.g., zeolite, and provides additional body to the composition to cover wrinkle lines. Zeolite enhances the overall properties of the composition, namely the smoothing effect, texture, spreadability and rheological properties; as well as shortening the drying time following application of the composition. Fillers containing zeolite are added in an amount of from about 1 to about 10%, preferably from about 2 to about 7.5%, of the total composition based on 100% solids. A preferred zeolite is commercially available from PQ Corp. marketed under the name Valfor ® Z81-352 (hydrated Na-X aluminosilicate zeolite powder). Zeolite is added in an amount of from about 1 to about 8%, and preferably from about 2 to about 6%, of the total composition based on 100% solids. Suitable filler additives include ultrafine particulate microcrystalline, e.g., microcrystallinecellulose. Ultrafine microcrystalline cellulose, commercially available from FMC Corp. marketed under the name Avicel ® RC-591, is used in combination with zeolite. Microcrystalline cellulose is added in an amount of from about 0.25 to about 2.0%, preferably from about 1 to about 1.5%, of the total composition based on 100% solids. Microcrystalline cellulose further extends the surface area of the pigments and aids in increasing the hiding power of the composition. Microcrystalline cellulose is an efficient thixotropic thickener and consequently, its concentration must be regulated to prevent undesirable gelation which may reduce spreadability of the composition. Typically, microcrystalline cellulose is added in amounts which equal the highest concentration that permits good flow.

The wrinkle masking composition can also include pigments which provide skin color matching and additional hiding power. Suitable pigments include titanium dioxide ($TiO_2$), added primarily for hiding power, and iron oxides, added primarily for skin color matching. Commercially available pigments can be obtained from Hilton Davis Drug & Cosmetic Pigment, Inc., marketed under the names Lo-Micron Yellow ® (10-34-PA-2576) and Lo-Micron Umber ® (10-34-PA-2736). Pigmentation is added in an amount of from about 5 to about 15%, preferably from about 8 to about 10%, of the total composition based on 100% solids.

Acrylic acid polymer can be added in small amounts of from about 0.05 to about 0.2%, preferably about 0.1%, of the total composition based on 100% solids, as an additional film forming and rheology control agent. Carbopol ® 941 (acrylic acid polymer mol. wt. 1.25 M) is commercially available from B. F. Goodrich.

Additives such as the lysine derivative Amihope-LL ® can be present at very low levels to help blend and hold the components together to form a smooth flexible membrane that molds to the surface of the skin. Amihope-LL ® provides cohesive power and aids in the smooth spreading of the composition. Amihope-LL ® (L-lysine and lauric acid powder-Ajinomoto, Co.) is commercially available from Centerchem, Inc. Lysine derivatives are a preferred ingredient of the composition added in an amount of from about 0.05 to about 0.1%, preferably from about 0.07 to about 0.08%, of the total composition based on 100% solids. Other additives can be used as needed for special effects, such as the use of a hydantoin for healing and soothing of the skin. Optional ingredients include the hydantoin Allantoin, which is commercially available from Centerchem, Inc.

Suitable preservatives include Lexgard ® M (methylparaben), available from Inslex Chemical Co.; Kathon CG, available from Rohm and Hass Co.; and Germall ® 115, available from Sutton Laboratories.

Water is added to provide the proper compositional balance. The wrinkle masking composition of the present invention is an aqueous composition, yet after applying to skin the composition dries to a film which is sufficiently resistant to water and thus prevents unintended removal by tears or perspiration. However, the dried composition is completed removed from the skin by simple soap and water.

Clinical studies of the wrinkle-masking composition of the present invention were conducted as follows:

Each participant cleaned her face with a commercial cleanser using a cotton pad and allowed her face to air dry for twenty minutes.

Each participant applied a small amount of the wrinkle masking composition on the right side of her face between the eye and the jaw using a rotating and rubbing motion with her fingertips. The masking gel was allowed to air dry.

Each participant chose and applied on both sides of her face a liquid makeup foundation from one of two shades. The foundation air dried for five minutes.

A cotton pad was used to apply a setting powder over the foundation using a gentle, puffing action. The excess powder was brushed off with a camel hair brush.

Each participant chose and applied rouge from three different powders using a camel hair brush.

Each participant was allowed to resume her regular workday activity.

After approximately 6 hours, each participant cleaned her face with one of two commercial lotions.

The results confirm that the composition of the present invention is easy to apply and rapidly dries to a satisfactory texture. The dried composition effectively covers the fine line wrinkles of the face and makeup can easily be applied to it. The composition/makeup two-layer system maintained its integrity for over six hours upon which time the material was easily removed. The composition is resistant to skin secretion which enhances the long wearing capabilities of the composition. By molding to the skin the underlying film composition adapted well to skin expressions and movements without cracking or peeling. The composition of the present invention can be provided in a neutral shade or light or dark skin colors to be color compatible with various makeup shades. The aforementioned tests illustrate that aqueous based commercial liquid makeups that are favored by the user and match their type and shade of skin are compatible with the wrinkle masking composition of the present invention. A large number of commercial makeups are compatible, however, others contain a vehicle which can attack and remove the wrinkle masking layer. A conventional setting powder can also be applied directly over the wrinkle masking composition or over the makeup. The wrinkle masking composition provides a comfortable and pleasant cosmetic by allowing the skin to breathe.

The following Examples illustrate prior art compositions of wrinkle smoothers. These comparative examples were made in accordance with techniques known to one skilled in the art.

COMPARATIVE EXAMPLE A
R.I. VANDERBUILT'S FORMULA #339
FOR A GENERAL PURPOSE WRINKLE SMOOTHER

| Composition* | Parts by weight (pbw) in grams (g) |
|---|---|
| Veegum ® | 1.5 |
| CMC-7LF ® | 1.0 |
| Distilled Water | 82.5 |
| Flexan ® 130 (30% Na-Polystyrene sulfonate) | 12.0 |
| Collasol ® (Soluble Collagen) | 3.0 |
| Germaben II ® (10% aqueous soln.) | 0.7 |
| TOTAL | 100.7 |

COMPARATIVE EXAMPLE B
COMPOSITIONS BASED ON U.S. PAT. NO. 4,362,715
(EXAMPLES 1 AND 7) AS WRINKLE SMOOTHERS

| | Parts by weight (pbw) in grams | |
|---|---|---|
| | (i) Ex. #1 of '715 | (ii) Ex. #7 of '715 |
| Carbopol ® 941 | 0.4 | 0.04 |
| Valfor ® Z81-352 | 10.0 | 1.00 |
| CMC-7MF ® | — | 3.00 |
| Propylene Glycol | — | 1.00 |
| Distilled Water | 89.6 | 94.96 |
| TOTAL | 100.0 | 100.0 |

Note: Comparative Example B(i) was the basic gel used to formulate Comparative Example B(ii).
*Note: Each ingredient represents 100% solids unless otherwise noted.

TABLE I
SUPPLIERS OF CHEMICALS AND BIOLOGICALS
FOR FILM SMOOTHERS USED IN
COMPARATIVE EXAMPLES A AND B

| Materials | Supplier |
|---|---|
| Carbopol ® 941 (mol wt 1.25M) (acrylic acid polymer) | B. F. Goodrich |
| Collasol ® (soluble animal collagen) | Croda Inc. |
| CMC-7LF ® (low visc. pharm grade) (sodium carboxymethyl cellulose) | Hercules Inc. |
| CMC-7MF ® (med visc. pharm grade) (sodium carboxymethyl cellulose) | Hercules Inc. |
| Flexan ® 130 (30% solids) (sodium salt, polystyrene sulfonate) | National Starch and Chemical Corporation |
| Valfor ® Z81-352 (hydrated Na-X zeolite aluminosilicate powder) | PQ Corporation |
| Veegum ® (purified smectite clay) (colloidal magnesium aluminum silicate) | R. T. Vanderbuilt Co. Inc. |
| Germaben ® II 10% aqueous solution | Sutton Laboratories |
| Propylene glycol (USP-FCC grade) | Union Carbide Inc. |

The composition of Comparative Example A produced a translucent, whitish lotion having a pH of from about 7.5 to about 8.0. The composition of Comparative Example B(i) produced a gel having a pH of about 8.3. The films resulting from the compositions of Comparative Examples A and B exhibited mechanical problems; they were brittle and cracked with skin motion. The prior art compositions formed thin, smooth films that tightened the skin but did not hide fine wrinkles.

The following Examples illustrate preferred embodiments of the wrinkle masking composition of the present invention.

The gel of the present invention was made by mixing a plasticizer for the polymeric matrix, propylene glycol hexylene glycol and glycerin; a film forming polymer, CMC; a filler containing Zeolite, Valfor ® Z81-352 and Avicel ®; pigmentation, titanium dioxide, Amihope ®; additional additives and water by a conventional method known to those skilled in the art under conditions of high energy and heat. The heated mixture was cooled and the biopolymeric modifier, hyaluronic acid (1%), Dermasaccarides ® LS-ST (12%), elastin, and collagen and a film forming polymer, Flexan ® (30%) were added. The cosmetic mixture was prepared according to techniques known to one skilled in the art.

EXAMPLE 1

WRINKLE MASKING GELS - UNPIGMENTED

| Composition* | A g (pbw) | B g (pbw) | C g (pbw) |
|---|---|---|---|
| Flexan ® 130 (30%) | 2.43 | 2.31 | 2.22 |
| CMC-7MF ® | 2.43 | 2.31 | 2.22 |
| Propylene Glycol | 4.05 | 3.86 | 3.70 |
| Glycerin | 6.49 | 6.18 | 5.91 |
| Hexylene glycol | 1.22 | 1.16 | 1.10 |
| Hyaluronic Acid (1%) | 0.81 | 0.77 | 0.74 |
| Pancogene ® - S (0.3%) | 4.05 | 3.86 | 3.70 |
| Hydrolastan ® (10%) | — | 4.76 | 4.76 |
| Dermosaccharides ® LS-ST (12%) | — | — | 4.04 |
| Avicel ® RC-591 | 1.62 | 1.54 | 1.48 |
| Valfor ® Z81-352 | 2.03 | 1.93 | 1.85 |
| Amihope ® - LL | 0.08 | 0.08 | 0.08 |
| Carbopol ® 941 | 0.08 | 0.08 | 0.08 |
| Kathon ® CG | 0.65 | 0.62 | 0.59 |
| Distilled Water | 74.06 | 70.54 | 67.53 |
| TOTAL | 100 | 100 | 100 |

*Note: Each ingredient represents 100% solids unless otherwise noted.

Examples 1 (A–C) yielded compositions having acceptable spreadability, texture, feel, flexibility and ability to fill and cover wrinkles.

EXAMPLE 2

WRINKLE MASKING GELS - PIGMENTED

| Composition* | kg | Pbw as Used | 100% Solids |
|---|---|---|---|
| Flexan ® 130 (30%) | 2.50 | 2.08 | 0.62 |
| CMC-7MF ® | 2.25 | 1.87 | 1.87 |
| Propylene Glycol | 4.00 | 3.33 | 3.33 |
| Glycerin | 14.00 | 11.66 | 11.66 |
| Hexylene glycol | 3.00 | 2.50 | 2.50 |
| Hyaluronic Acid (1%) | 1.00 | 0.83 | 0.008 |
| Pancogene ® - S (0.3%) | 4.00 | 3.33 | 0.01 |
| Hydrolastan ® (10%) | 5.00 | 4.17 | 0.41 |
| Dermosaccharides ® LS-ST (12%) | 6.00 | 5.00 | 0.60 |
| Avicel ® RC-591 | 1.50 | 1.25 | 1.25 |
| Valfor ® Z81-352 | 2.00 | 1.67 | 1.67 |
| Amihope ® - LL | 0.08 | 0.07 | 0.07 |
| Carbopol ® 941 | 0.10 | 0.08 | 0.08 |
| Titanium dioxide | 9.00 | 7.50 | 7.50 |
| Lo-Micron Umber ® BC(10-34-PA-2736) | 1.20 | 1.00 | 1.00 |
| Lo-Micron Yellow ® BC(10-34-PA-1576) | 0.80 | 0.67 | 0.67 |
| Allantoin | 0.50 | 0.42 | 0.42 |
| Germall ® 115 | 0.40 | 0.33 | 0.33 |
| Lexgard ® M | 0.20 | 0.17 | 0.17 |
| Distilled water | 62.50 | 52.07 | 65.83 |
| Total | 120.03 kg | 100 | 100 |

*Note: Each ingredient represents 100% solids unless otherwise noted.

Example 2 yielded a pigmented composition having increased hiding power and skin shade matching.

EXAMPLE 3

MODIFICATION OF THE FORMULATION DESCRIBED IN EXAMPLE 2

| Formulation | Hyaluronic Acid (1%) (g) | pbw | Dermosaccharides ® LS-ST (12%) (g) | pbw | Water (g) | pbw | pH |
|---|---|---|---|---|---|---|---|
| Composition of Example 2 | 1.00 | 0.83 | 6.00 | 5.00 | 62.50 | 52.07 | 6.79 |
| A | 0.75 | 0.62 | 6.00 | 5.00 | 62.75 | 52.28 | 6.72 |
| B | 0.50 | 0.42 | 6.00 | 5.00 | 63.00 | 52.49 | 6.70 |
| C | 1.00 | 0.83 | 5.00 | 4.17 | 63.50 | 52.90 | 6.78 |
| D | 1.00 | 0.83 | 4.00 | 3.33 | 64.50 | 53.74 | 6.68 |
| E | 1.00 | 0.83 | 3.00 | 2.50 | 65.50 | 54.57 | 6.76 |
| F | 0.87 | 0.72 | 5.50 | 4.58 | 63.13 | 52.60 | 6.76 |
| G | 0.75 | 0.62 | 5.50 | 4.58 | 63.25 | 52.70 | 6.73 |
| H | 0.87 | 0.72 | 4.50 | 3.75 | 64.13 | 53.43 | 6.73 |
| I | 0.75 | 0.62 | 4.50 | 3.75 | 64.25 | 53.53 | 6.72 |
| J | 0.50 | 0.42 | 3.00 | 2.50 | 66.00 | 54.99 | 6.78 |

Example 3 represents the composition according to Example 2 wherein the amounts of hyaluronic Acid (1%) and Dermosaccharides ® LS-ST (12%) are reduced to optimize the cost/performance relationship of the composition. The formulations of Example 3 were prepared in accordance with Example 2, except all ingredients were added in grams to a total of 120.03 grams. All of the compositions of Example 3 exhibited acceptable properties. Accordingly, suitable compositions were prepared including hyaluronic acid (1%) in a range from about 0.42 to about 0.83 pbw and Dermosaccharides ® LS-ST (12%) in a range of from about 2.5 to 5.0 pbw, of the total composition.

EXAMPLE 4

EFFECTS OF INCREASING CONCENTRATION OF THICKENER (VALFOR ® Z81-352) ON PHYSICAL PROPERTIES OF WRINKLE MASKING COMPOSITION DESCRIBED IN EXAMPLE 2

| Formulation | CMC-7MF ® (g) | pbw | Valfor ® (g) | pbw | Distilled Water (g) | pbw | pH |
|---|---|---|---|---|---|---|---|
| Composition of Example 2 | 2.25 | 1.87 | 2.00 | 1.67 | 62.50 | 52.07 | 6.79 |
| 4 | 2.25 | 1.87 | 6.00 | 5.00 | 58.50 | 48.73 | 7.10 |

The formulations of Example 4 were prepared in accordance with Example 2, except all ingredients were added in grams to a total of 120.03 grams. Increasing the amount of zeolite from about 1.67 to about 5.0 pbw, as shown in Example 4, yielded a gel having improved texture, appearance and spreading properties. The film drying time was considerably reduced, depending on the film thickness, from about 5 minutes, for the basic formulation of Example 2, to between about 0.5 to about 2.0 minutes for the Example 4 formulation. The resultant film exhibited excellent fine-line masking. Formulation 4 is a preferred embodiment and exhibits excellent overall performance.

COMPARATIVE EXAMPLE C

EFFECTS OF INCREASING CONCENTRATION OF THICKENER (CMC-7MF ®), ON PHYSICAL PROPERTIES OF WRINKLE MASKING COMPOSITION DESCRIBED IN EXAMPLE 2

| Formulation | CMC-7MF ® (g) | pbw | Valfor ® (g) | pbw | Distilled Water (g) | pbw | pH |
|---|---|---|---|---|---|---|---|
| Composition of Example 2 | 2.25 | 1.87 | 2.00 | 1.67 | 62.50 | 52.07 | 6.79 |
| C (Comparative | 4.50 | 3.74 | 2.00 | 1.67 | 60.25 | 50.19 | 6.37 |

| COMPARATIVE EXAMPLE C EFFECTS OF INCREASING CONCENTRATION OF THICKENER (CMC-7MF ®), ON PHYSICAL PROPERTIES OF WRINKLE MASKING COMPOSITION DESCRIBED IN EXAMPLE 2 | | | | | | | |
|---|---|---|---|---|---|---|---|
| | CMC-7MF ® | | Valfor ® | | Distilled Water | | |
| Formulation | (g) | pbw | (g) | pbw | (g) | pbw | pH |
| Example) | | | | | | | |

The formulations of Comparative Example C were prepared in accordance with Example 2, except all ingredients were added in grams to a total of 120.03 grams. Comparative Example C represents a composition having the amount of carboxymethyl cellulose increased to about 3.74 pbw, which caused the gel to thicken and become a nonflowable paste.

Other objects, features and advantages of the present invention will become apparent from the foregoing detailed description and accompanying examples. It should be understood, however, that the detailed description and specific examples, while indicating embodiments of the invention, are given by way of illustration only, since various changes and modifications within the spirit and scope of the invention will become apparent to those skilled in the art from this detailed description.

What is claimed is:

1. A wrinkle masking composition comprising:
   (a) a film forming water soluble polymer comprising sodium polystyrene sulfonate compatible with skin, which forms a basic matrix holding together said composition over skin and having adhesive properties to skin;
   (b) a plasticizer for said polymeric matrix,
   (c) a biopolymeric modifier which imparts skin-like character, skin compatibility and flexibility to said composition, and
   (d) a filler comprising aluminosilicate.

2. A wrinkle masking composition comprising:
   0.729% sodium polystyrene sulfonate
   2.43% carboxymethyl cellulose
   11.76% plasticizer
   0.008% hyaluronic acid
   0.012% collagen
   2.03% aluminosilicate
   1.62% microcrystalline cellulose
   0.08% acrylic acid polymer
   0.08% mixture of L-lysine and lauric acid
   q.s. water, the total composition based on 100% solids.

3. The composition according to claim 1, wherein said film forming polymer further comprises carboxymethyl cellulose, cellulosic ether, or polyvinylpyrrolidone polymer.

4. The composition according to claim 1, wherein said polymer plasticizer is a member selected from the group consisting of glycols, polyols, glycerin and mixtures thereof.

5. The composition according to claim 1, wherein said biopolymeric modifier is a member selected from the group consisting of hyaluronic acid, elastin, collagen, polysaccharide, glycosaminoglycan and mixtures thereof.

6. The composition according to claim 1, wherein said filler further comprises microcrystalline cellulose.

7. The composition according to claim 1, wherein said film forming polymer comprises from about 1.3 to about 4.8% of the total composition based on 100% solids.

8. The composition according to claim 1, wherein said film forming polymer comprises from about 2.1 to about 3% of the total composition based on 100% solids.

9. The composition according to claim 1, wherein said film forming polymer comprises sodium polystyrene sulfonate in an amount of from about 0.3 to about 1.8% of the total composition based on 100% solids.

10. The composition according to claim 1, wherein said film forming polymer comprises sodium polystyrene sulfonate in an amount of from about 0.6 to about 0.75% of the total composition based on 100% solids.

11. The composition according to claim 2, wherein said film forming polymer further comprises carboxymethyl cellulose in an amount of from about 1 to about 3% of the total composition based on 100% solids.

12. The composition according to claim 2, wherein said film forming polymer further comprises carboxymethyl cellulose in an amount of from about 1.5 to about 2.25% of the total composition based on 100% solids.

13. The composition according to claim 1, wherein said polymer plasticizer comprises an amount of from about 10 to about 30% of the total composition based on 100% solids.

14. The composition according to claim 1, wherein said polymer plasticizer comprises an amount of from about 15 to about 25% of the total composition based on 100% solids.

15. The composition according to claim 1, wherein said biopolymeric modifier as 100% solids comprises from about 0.0025 to about 1.94% of said composition.

16. The composition according to claim 1, wherein said biopolymeric modifier as 100% solids comprises from about 0.0075 to about 1.25% of said composition.

17. The composition according to claim 1, wherein said biopolymeric modifier comprises hyaluronic acid in an amount of from about 0.0025 to about 0.02% of the total composition based on 100% solids.

18. The composition according to claim 1, wherein said biopolymeric modifier comprises hyaluronic acid in an amount of from about 0.005 to about 0.0125% of the total composition based on 100% solids.

19. The composition according to claim 1, wherein said biopolymeric modifier comprises hyaluronic acid in an amount of from about 0.0075 to about 0.01% of the total composition based on 100% solids.

20. The composition according to claim 1, wherein said biopolymeric modifier comprises elastin in an amount of from about 0.1 to about 0.7% of the total composition based on 100% solids.

21. The composition according to claim 1, wherein said biopolymeric modifier comprises elastin in an amount of from about 0.2 to about 0.6% of the total composition based on 100% solids.

22. The composition according to claim 1, wherein said biopolymeric modifier comprises elastin in an amount of from about 0.4 to about 0.5% of the total composition based on 100% solids.

23. The composition according to claim 1, wherein said biopolymeric modifier comprises collagen in an amount of from about 0.003 to about 0.021% of the total composition based on 100% solids.

24. The composition according to claim 1, wherein said biopolymeric modifier comprises collagen in an amount of from about 0.006 to about 0.018% of the total composition based on 100% solids.

25. The composition according to claim 1, wherein said biopolymeric modifier comprises collagen in an amount of from about 0.009 to about 0.015% of the total composition based on 100% solids.

26. The composition according to claim 1, wherein said biopolymeric modifier comprises polysaccharide and glycosaminoglycans in an amount of from about 0.24 to about 1.2% of the total composition based on 100% solids.

27. The composition according to claim 1, wherein said biopolymeric modifier comprises polysaccharide and glycosaminoglycans in an amount of from about 0.36 to about 0.96% of the total composition based on 100% solids.

28. The composition according to claim 1, wherein said biopolymeric modifier comprises polysaccharide and glycosaminoglycans in an amount of from about 0.6 to about 0.72% of the total composition based on 100% solids.

29. The composition according to claim 1, wherein said filler comprises an amount of from about 1.25 to about 10% of the total composition based on 100% solids.

30. The composition according to claim 1, wherein said filler comprises sodium aluminosilicate in an amount of from about 1 to about 8% of the total composition based on 100% solids.

31. The composition according to claim 1, wherein said filler comprises sodium aluminosilicate in an amount of from about 2 to about 6% of the total composition based on 100% solids.

32. The composition according to claim 1, wherein said filler comprises microcrystalline cellulose in an amount of from about 0.25 to about 2.0% of the total composition based on 100% solids.

33. The composition according to claim 1, wherein said filler comprises microcrystalline cellulose in an amount of from about 1 to about 1.5% of the total composition based on 100% solids.

34. The composition according to claim 1, further comprising pigmentation.

35. The composition according to claim 34, wherein said pigmentation is a member selected from the group consisting of titanium dioxide, iron oxide and mixtures thereof.

36. The composition according to claim 34, wherein said pigmentation comprises an amount of from about 5 to about 15% of the total composition based on 100% solids.

37. The composition according to claim 34, wherein said pigmentation comprises an amount of from about 8 to about 10% of the total composition based on 100% solids.

38. The composition according to claim 1, further comprising a rheology control agent.

39. The composition according to claim 1, further comprising a binder for said composition.

40. The composition according to claim 39, wherein said binder comprises L-lysine and lauric acid.

41. The composition according to claim 40, wherein said binder comprises an amount of from about 0.05 to about 0.1% of the total composition based on 100% solids.

42. The composition according to claim 40, wherein said binder comprises an amount of from about 0.07 to about 0.08% of the total composition based on 100% solids.

43. The composition according to claim 1, further comprising a preservative.

44. A cosmetic composition comprising:
  (a) a first layer comprising a wrinkle masking composition comprising a film forming polymer which forms a matrix, a plasticizer for said polymeric matrix, a biopolymeric modifier and a filler comprising aluminosilicate; and
  (b) a second layer comprising a makeup compatible with said first layer, said second layer covering said first layer.

45. The composition according to claim 44, further comprising a third layer comprising a setting powder, said third layer covering said second layer or being between said first and second layers.

46. A process for the filling, covering or masking of fine line wrinkles of the skin comprising the steps of:
  (a) applying to the skin a first layer comprising a wrinkle masking composition comprising a film forming polymer, a plasticizer for said polymer in matrix, a biopolymeric modifier and a filler comprising aluminosilicate; and
  (b) applying to said first layer a layer comprising a makeup compatible with said first layer.

47. The process according to claim 46, further comprising the step of applying to said second layer a third layer comprising a setting powder.

48. The composition according to claim 44, wherein said wrinkle masking composition comprises:
  0.729% sodium polystyrene sulfonate
  2.43% carboxymethyl cellulose
  11.76% plasticizer
  0.008% hyaluronic acid
  0.012% collagen
  2.03% aluminosilicate
  1.62% microcrystalline cellulose
  0.08% acrylic acid polymer
  0.08% mixture of L-lysine and lauric acid
  q.s. water, the total composition based on 100% solids.

49. The process according to claim 46, wherein said wrinkle masking composition comprises:
  0.729% sodium polystyrene sulfonate
  2.43% carboxymethyl cellulose
  11.76% plasticizer
  0.008% hyaluronic acid
  0.012% collagen
  2.03% aluminosilicate
  1.62% microcrystalline cellulose
  0.08% acrylic acid polymer
  0.08% mixture of L-lysine and lauric acid
  q.s. water, the total composition based on 100% solids.

* * * * *

UNITED STATES PATENT AND TRADEMARK OFFICE
CERTIFICATE OF CORRECTION

PATENT NO.   : 4,965,071

DATED        : Oct. 23, 1990

INVENTOR(S)  : Antoine Kawam

It is certified that error appears in the above-identified patent and that said Letters Patent is hereby corrected as shown below:

On the title page, under item [19] and in item [75], "Kawan", the inventor's last name, should be corrected to read --Kawam--.

Signed and Sealed this

Third Day of November, 1992

Attest:

DOUGLAS B. COMER

Attesting Officer

Acting Commissioner of Patents and Trademarks